US008778413B2

(12) United States Patent
Usansky et al.

(10) Patent No.: US 8,778,413 B2
(45) Date of Patent: Jul. 15, 2014

(54) DOSING REGIMENS AND METHODS OF TREATMENT USING CARBON MONOXIDE

(75) Inventors: Helen H. Usansky, Hillsborough, NJ (US); Khurram Jamil, Langhorne, PA (US)

(73) Assignee: Ikaria, Inc., Hampton, NJ (US)

( * ) Notice: Subject to any disclaimer, the term of this patent is extended or adjusted under 35 U.S.C. 154(b) by 168 days.

(21) Appl. No.: 13/106,437

(22) Filed: May 12, 2011

(65) Prior Publication Data
US 2011/0280966 A1 Nov. 17, 2011

Related U.S. Application Data

(60) Provisional application No. 61/334,755, filed on May 14, 2010.

(51) Int. Cl.
*A61K 9/12* (2006.01)
*A01N 1/02* (2006.01)
(52) U.S. Cl.
USPC ............. 424/699; 514/789; 435/1.1; 436/134
(58) Field of Classification Search
USPC ............. 424/699; 514/789; 436/134; 435/1.1
See application file for complete search history.

(56) References Cited

U.S. PATENT DOCUMENTS

| | | | | |
|---|---|---|---|---|
| 7,364,757 | B2 * | 4/2008 | Otterbein et al. | 424/699 |
| 8,128,962 | B2 * | 3/2012 | Blackman | 424/613 |
| 8,128,963 | B2 * | 3/2012 | Pinsky et al. | 424/699 |
| 2003/0068387 | A1 * | 4/2003 | Buelow et al. | 424/699 |
| 2003/0219496 | A1 * | 11/2003 | Otterbein et al. | 424/699 |
| 2006/0093681 | A1 * | 5/2006 | Krebs et al. | 424/699 |

OTHER PUBLICATIONS

Favory et al., "Myocardial Dysfunction and Potential Cardiac Hypoxia in Rats Induced by Carbon Monoxide Inhalation," 2006, J. of Respiratory and Critical Care Medicine, 174(3): 320-325.*
Guo et al., "Administration of a CO-releasing molecule at the time of reperfusion reduces infarct size in vivo," 2004, Am. J. Physiol. Heart Cir. Physiol., 286(No. 5, Pt. 2):H1649-1653.*
Hangai-Hoger et al., "Microvascular and systemic effects following top load administration of saturated carbon monoxide-saline solution," 2007, Crit. Care Med., 35(4):1123-1132.*
Prockop et al., "Carbon monoxide intoxication: An updated review," 2007, J. of the Neurological Sciences, 2612:122-130.*
R.D. Stewart, "The effect of carbon monoxide on humans," 1976, J. of Occupational Medicine, 18(5): 304-309; Abstract only.*
R.D. Stewart, "The Effect of Carbon Monoxide on Humans," May 1976, Journal of Occupational Medicine, 18(5): 304-309.*
Hangai-Hoger et al., "Microvascular and systemic effects following top load administration of saturated carbon monoxide-saline solution," 2007, Critical Care Medicine, 35(4):1123-1132.*
Favory et al., "Myocardial Dysfunction and Potential Cardiac Hypoxia in Rats Induced by Carbon Monoxide Inhalation," 2006, J. of Respiratory and Critical Care Medicine, 174(3):320-325.*
Guo et al., "Administration of a CO-releasing molecule at the time of reperfusion reduces infarct size in vivo," 2004, Am. J. Physiology, 286(No. 5, Pt.2):H1649-1653.*
Prockop et al., "Carbon monoxide intoxication: An updated review," 2007, J. of the Neurological Sciences, 262:122-130.*
R.D. Stewart, "The effect of carbon monoxide on humans," 1976, J. of Occupational Medicine, 18(5):304-309.*

* cited by examiner

*Primary Examiner* — Jane C Oswecki
(74) *Attorney, Agent, or Firm* — Hoffmann & Baron, LLP

(57) ABSTRACT

The present invention is directed to dosing regimens for the administration of carbon monoxide in the treatment of various indications as well as methods for enhancing organ function following transplant thereof.

5 Claims, 7 Drawing Sheets

US 8,778,413 B2

DOSING REGIMENS AND METHODS OF TREATMENT USING CARBON MONOXIDE

CROSS REFERENCE TO RELATED APPLICATION

This application claims the benefit of U.S. Provisional Application No. 61/334,755, filed May 14, 2010, the contents of which are incorporated by reference herein.

FIELD OF THE INVENTION

The present invention relates to dosing regimens for the administration of carbon monoxide in the treatment of various indications as well as methods for enhancing organ function following transplant thereof.

BACKGROUND OF THE INVENTION

Carbon monoxide, naturally produced by the human body, is toxic at high concentrations as it binds to hemoglobin to form carboxyhemoglobin (COHb) which is ineffective for delivering oxygen to bodily tissues. Paradoxically, carbon monoxide has been shown to be a signaling molecule with various therapeutic effects, such as cytoprotection, anti-inflammation and immunosuppression. When given at appropriate doses, carbon monoxide can be clinically beneficial for treating various indications including ischemia reperfusion injury. There is a medical need for identifying dosing regimens for the administration of carbon monoxide that are therapeutic while minimizing the risk of adverse effects associated with administration of the same.

SUMMARY OF INVENTION

The present invention provides clinical evidence of carbon monoxide preserving organ functions after transplantation and potential dosing regimens of carbon monoxide for treatment of various indications that are related to ischemia-reperfusion injury (e.g., organ transplant surgeries, vascular interventional procedures, various cardiovascular diseases, etc.). The therapeutic efficacy of carbon monoxide is dose-dependent, that is, the higher the dose the greater the effect.

In one aspect of the invention, there is provided methods for treating a patient in need thereof with carbon monoxide, including administering to the patient an effective amount of carbon monoxide that results in a carboxyhemoglobin concentration of at least 3%. In one embodiment, the carboxyhemoglobin concentration is between about 3% and about 15%, where a positive dose-related trend on preservation of renal functions is observed without negative impact on cardiovascular and neurocognitive functions.

In one embodiment, the patient is administered a single dose of carbon monoxide during surgery at 2 mg/kg or 3 mg/kg for a sufficient time period that results in effective carboxyhemoglobin concentrations during surgery.

In one embodiment, the patient is administered carbon monoxide at the time of vascular reperfusion. In one embodiment, the carboxyhemoglobin concentration is between about 7% and about 15%.

In one embodiment, the organ is selected from kidney, liver, heart, skin, large or small intestine and pancreas. In one embodiment, the organ is kidney. In one embodiment, kidney function is improved as indicated by an improvement of renal function (e.g., serum creatinine level and glomerular filtration rate).

In one embodiment of any of the aforementioned methods, carbon monoxide is administered to the patient in a gaseous form, a liquid form, or a combination thereof.

In one embodiment of any of the aforementioned methods, an additional agent that has a therapeutic effect is administered to the patient.

BRIEF DESCRIPTION OF THE DRAWINGS

Figure 5:
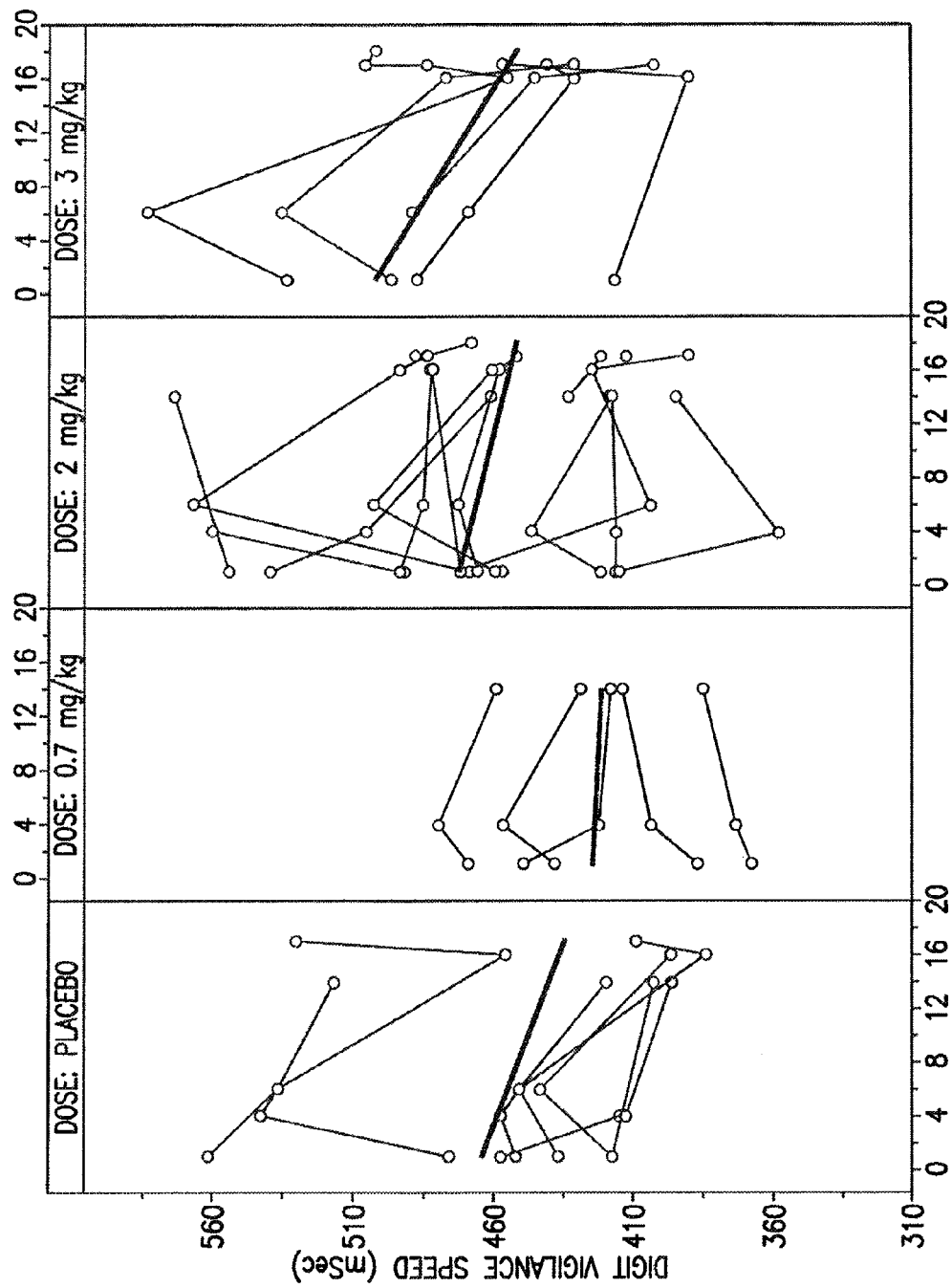
Figure 6:
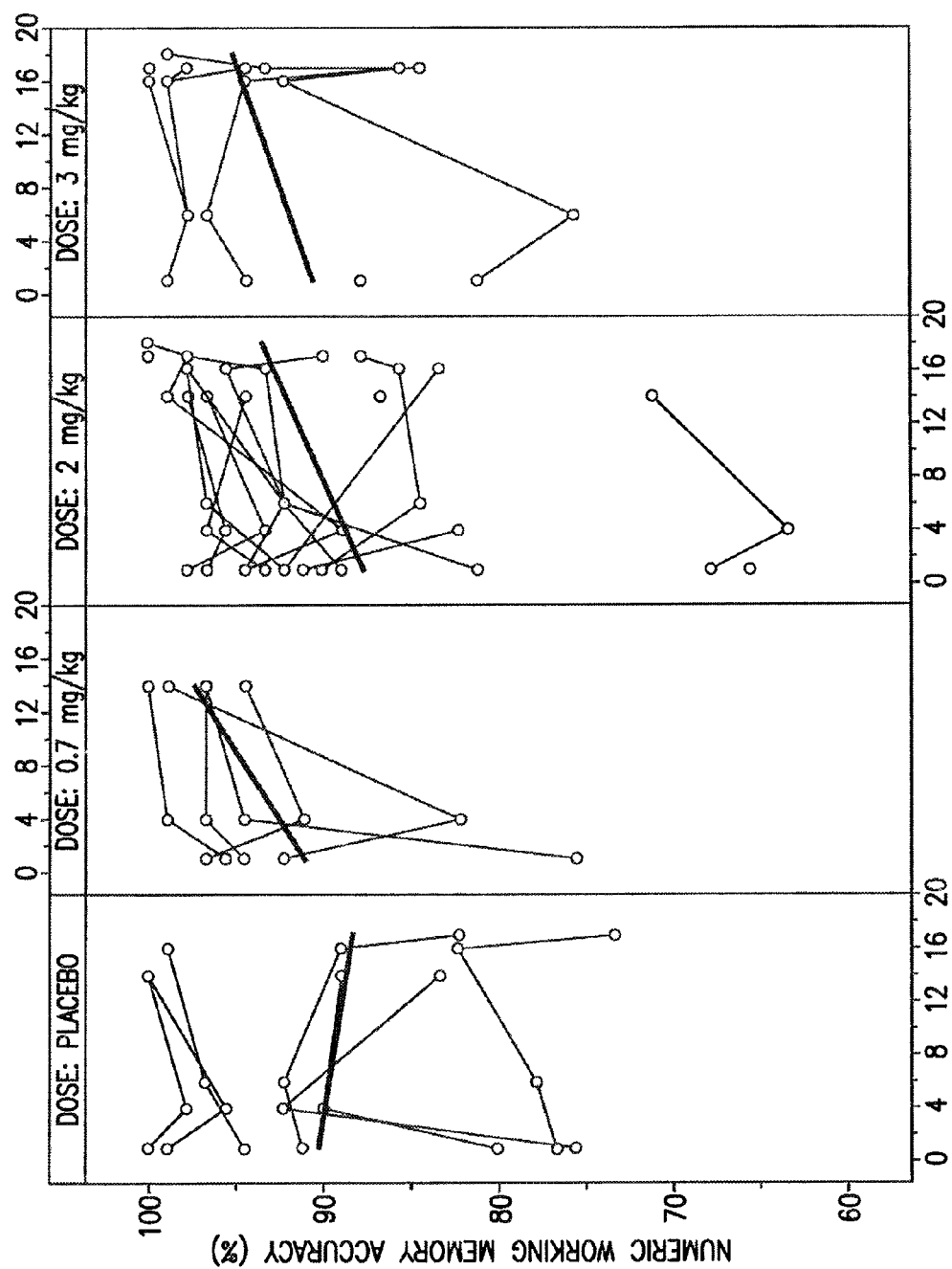
Figure 7:
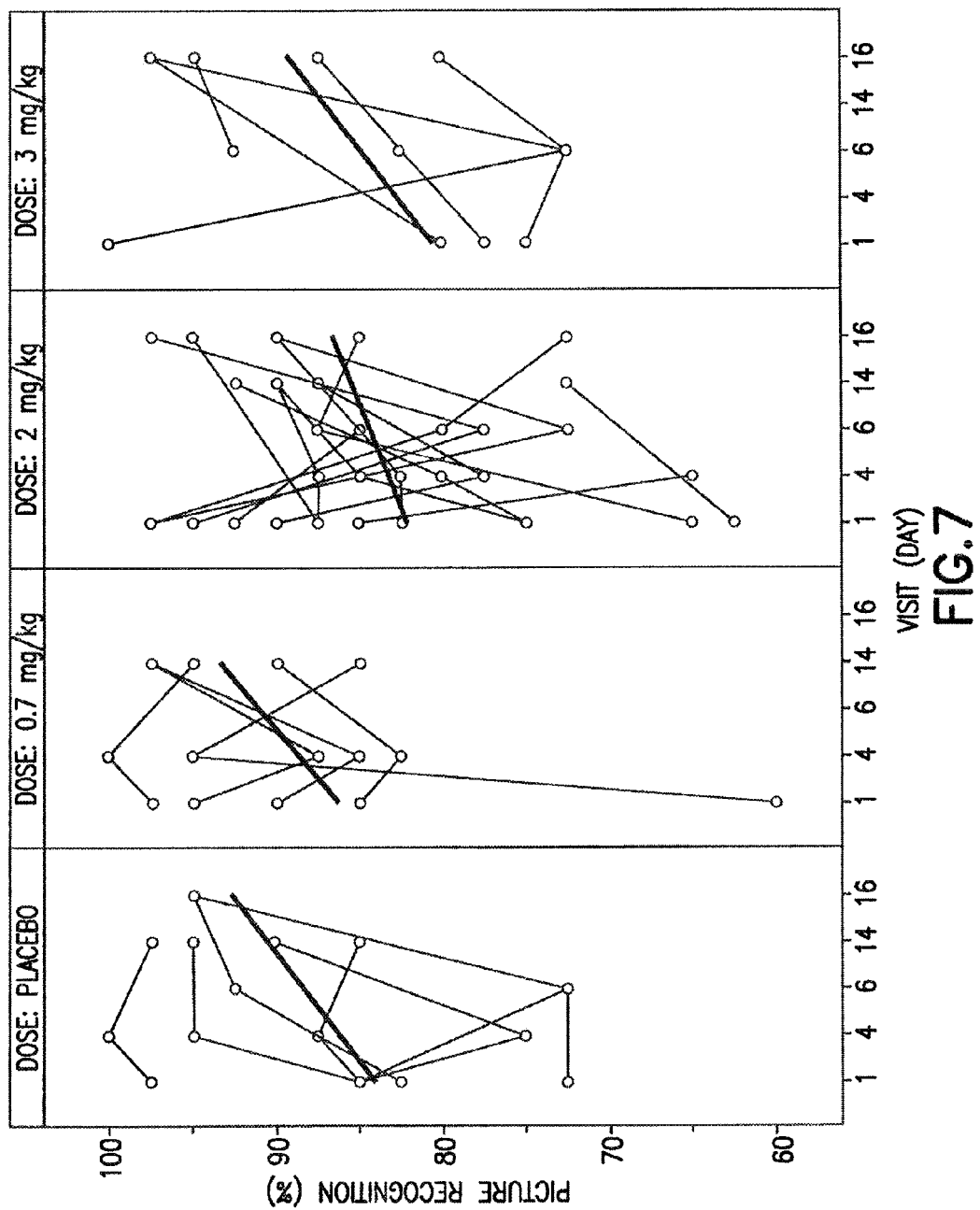

FIG. 5, FIG. 6 and FIG. 7 illustrate the impact of carbon monoxide treatment on neurocognitive functions over 6 months in subjects receiving kidney transplants following inhalation of placebo, 0.7 mg/kg, 2 mg/kg or 3 mg/kg carbon monoxide through the evaluation of individual digit vigilance speed (FIG. 5), numeric working memory accuracy (FIG. 6) and picture recognition (FIG. 7). The CO doses were administered either 12-48 hours post-operatively following renal transplant (placebo, 0.7 mg/kg or 2 mg/kg) or intra-operatively during renal transplant surgery (placebo, 2 mg/kg or 3 mg/kg). Visit #1: Screening; Visit #4: Day 0; Visit #6: Day 1; Visit #14-16: Day 28; Visit #17-18: Follow-up Weeks 16-24. The open symbols reflect individual observations, the thin lines reflect individual trends and thick lines reflect the average trend based on linear regression. The average trends demonstrate that carbon monoxide at a dose level up to 3 mg/kg does not have negative impact on neurocognitive functions.

DETAILED DESCRIPTION OF THE INVENTION

As used herein the following terms shall have the definitions set forth below.

As used herein, the term "treating" refers to the treatment of a disease or condition of interest in a patient (e.g., a mammal) having the disease or condition of interest, and includes, for example:
(i) preventing the disease or condition from occurring in a mammal, in particular, when such mammal is predisposed to the condition but has not yet been diagnosed as having it;
(ii) inhibiting the disease or condition (i.e., arresting its development);
(iii) reducing the extent of disease or condition (i.e., causing regression of the disease or condition); or
(iv) ameliorating the symptoms resulting from the disease or condition (i.e., relieving pain without addressing the underlying disease or condition). As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

As used herein, the term "patient" refers to an animal, human or non-human, to whom treatment according to the methods of the present invention is provided. Veterinary applications are clearly anticipated by the present invention. The term "patient" includes but is not limited to birds, reptiles, amphibians, and mammals, e.g., humans, other primates, pigs, rodents such as mice and rats, rabbits, guinea pigs, hamsters, cows, horses, cats, dogs, sheep and goats.

As used herein, the term "carbon monoxide" refers to molecular-carbon monoxide in its gaseous state, compressed into liquid form, or dissolved in aqueous solution.

As used herein, the term "administering" refers to any mode of transferring, delivering, introducing or transporting carbon monoxide or other agent to a subject. Administration of carbon monoxide or other agent may be conducted concurrently or sequentially in time. Additionally, administration of carbon monoxide and other agent(s) may be via the same or different route(s). Administration of carbon monoxide and other agent(s) may be performed via one or more of the following routes of administration: intravenous, intra-arterial, subcutaneous, intramuscular, intracisternal, intraperitoneal, intradermal, nasal via inhalation, nasal via aerosol, buccal, topical, intralesional, intracranial, intraprostatic, intrapleural, intratracheal, intranasal, intravitreal, intravaginal, intrarectal, intratumoral, intraocular, subconjunctival, intravesicular, mucosal, intrapericardial, intraumbilical, oral, local, by injection, by infusion, by continuous infusion, by absorption, by adsorption, by immersion, by localized perfusion, via a catheter, or via a lavage.

As used herein, the term "effective amount" refers to that amount of carbon monoxide which, when administered to a patient (e.g., a mammal) for a period of time is sufficient to cause an intended effect or physiological outcome. Effective amounts of carbon monoxide for use in the present invention include, for example, amounts that are effective for enhancing organ function following transplant thereof. The amount of carbon monoxide which constitutes an "effective amount" will vary depending on the condition and its severity, the manner of administration, and the patient (e.g., the age of the mammal to be treated), but can be determined routinely by one of ordinary skill in the art having regard to his own knowledge and to this disclosure. For example, in one embodiment, the term "effective amount" refers to the amount that can achieve a measurable result. In one embodiment, an "effective amount" is, for example, an amount that when administered to a human subject in need of medical treatment in a controlled Phase 2 or Phase 3 clinical trial produces a statistically significant benefit on a predefined clinical endpoint.

As used herein, the term "enhancing" refers to an increase in organ function following transplant. For example, with respect to a kidney transplant, enhancing includes an improvement in renal function as indicated by improvement in serum creatinine level or in glomerular filtration rate.

As used herein, the term "organ" refers to any anatomical part or member having a specific function in the animal. Further included within the meaning of this term are substantial portions of organs (e.g., cohesive tissues obtained from an organ). Such organs include but are not limited to kidney, liver, heart, skin, large or small intestine, pancreas, and lungs. Further included in this definition are bones and blood vessels (e.g., aortic transplants).

As used herein, the term "transplant" in the context of an organ transplant refers to the implanting of an organ, tissue, mass of cells, or individual cells into a patient. The term "transplantation" is defined in the art as the transfer of living tissues or cells from a donor to a recipient, with the intention of maintaining the functional integrity of the transplanted tissue or cells in the recipient (see, e.g., The Merck Manual, Berkow, Fletcher, and Beers, Eds., Merck Research Laboratories, Rahway, N.J., 1992). Transplants are categorized by site and genetic relationship between donor and recipient. The term includes autotransplantation (i.e., removal and transfer of cells or tissue from one location on a patient to the same or another location on the same patient), allotransplantation (i.e., transplantation between members of the same species), and xenotransplantation (i.e., transplantation between members of different species).

As used herein, the term "indications" includes ischemia-reperfusion injury including, but not limited to, organ transplant surgeries, vascular interventional procedures, and various cardiovascular diseases.

Preparation of Carbon Monoxide Compositions

A carbon monoxide composition may be a gaseous carbon monoxide composition. Compressed or pressurized gas useful in the methods of the invention can be obtained from any commercial source, and in any type of vessel appropriate for storing compressed gas. For example, compressed or pressurized gases can be obtained from any source that supplies compressed gases, such as oxygen, for medical use. The pressurized gas including carbon monoxide used in the methods of the present invention can be provided such that all gases of the desired final composition (e.g., CO and $O_2$, and optionally $N_2$, He, and/or $CO_2$) are mixed together in the same vessel. If desired, the methods of the present invention can be performed using multiple vessels containing individual gases. For example, a single vessel can be provided that contains carbon monoxide, with or without other gases, the contents of which can be optionally mixed with room air or with the contents of other vessels (e.g., vessels containing oxygen, nitrogen, carbon dioxide, compressed air, or any other suitable gas or mixtures thereof. Gaseous compositions administered to a patient according to the present invention typically contain 0% to about 79% by weight nitrogen, about 21% to about 100% by weight oxygen and about 0.0000001% to about 0.3% by weight (corresponding to about 0.001 ppm (i.e., 1 ppb) to about 3,000 ppm) carbon monoxide. Preferably, the amount of nitrogen in the gaseous composition is about 79% by weight, the amount of oxygen is about 21% by weight and the amount of carbon monoxide is about 0.0001% to about 0.25% by weight. The amount of carbon monoxide is preferably at least about 0.001%, e.g., at least about 0.005%, 0.01%, 0.02%, 0.025%, 0.03%, 0.04%, 0.05%, 0.06%, 0.08%, 0.10%, 0.15%, 0.20%, 0.22%, or 0.24% by weight. Preferred ranges of carbon monoxide include about 0.001% to about 0.24%, about 0.005% to about 0.22%, about 0.010% to about 0.20%, and about 0.015% to about 0.1% by weight.

A gaseous carbon monoxide composition may be used to create an atmosphere that comprises carbon monoxide gas. An atmosphere that includes appropriate levels of carbon monoxide gas can be created, for example, by providing a vessel containing a pressurized gas comprising carbon monoxide gas, and releasing the pressurized gas from the vessel into a chamber or space to form an atmosphere that includes the carbon monoxide gas inside the chamber or space. Alternatively, the gases can be released into an apparatus that culminates in a breathing mask or breathing tube, thereby creating an atmosphere comprising carbon monoxide gas in the breathing mask or breathing tube and ensuring the patient is the only person in the room exposed to significant levels of carbon monoxide.

Carbon monoxide levels in an atmosphere or a ventilation circuit can be measured or monitored using any method known in the art. Such methods include electrochemical detection, gas chromatography, radioisotope counting, infrared absorption, colorimetry, and electrochemical methods based on selective membranes (see, e.g., Sunderman et al., *Clin Chem,* 28:2026-2032 (1982); Ingi et al., *Neuron,* 16:835-842 (1996)). Sub-parts per million carbon monoxide levels can be detected e.g., by gas chromatography and radioisotope counting. Further, it is known in the art that carbon monoxide levels in the sub-ppm range can be measured in biological tissue by a midinfrared gas sensor (see, e.g., Morimoto et al., *Am J Physiol Heart Circ Physiol,* 280:H482-H488 (2001)). Carbon monoxide sensors and gas detection devices are widely available from many commercial sources.

A carbon monoxide composition may also be a liquid carbon monoxide composition. A liquid can be made into a carbon monoxide composition by any method known in the art for causing gases to become dissolved in liquids. For example, the liquid can be placed in a so-called "$CO_2$ incubator" and exposed to a continuous flow of carbon monoxide until a desired concentration of carbon monoxide is reached in the liquid. As another example, carbon monoxide gas can be "bubbled" directly into the liquid until the desired concentration of carbon monoxide in the liquid is reached. The amount of carbon monoxide that can be dissolved in a given aqueous solution increases with decreasing temperature. As still another example, an appropriate liquid may be passed through tubing that allows gas diffusion, where the tubing runs through an atmosphere comprising carbon monoxide (e.g., utilizing a device such as an extracorporeal membrane oxygenator). The carbon monoxide diffuses into the liquid to create a liquid carbon monoxide composition.

The liquid can be any liquid known to those of skill in the art to be suitable for administration to patients (see, for example, Oxford Textbook of Surgery, Morris and Malt, Eds., Oxford University Press, 1994). In general, the liquid will be an aqueous solution. Examples of solutions include Phosphate Buffered Saline (PBS), Celsior™ solution, Perfadex™ solution, Collins solution, citrate solution, and University of Wisconsin (UW) solution (Oxford Textbook of Surgery, Morris and Malt, Eds., Oxford University Press, 1994). The liquid compositions can include carbon monoxide at concentrations in the range of about 0.0001 to about 0.0044 g CO/100 g liquid, e.g., at least 0.0002, 0.0004, 0.0006, 0.0008, 0.0010, 0.0013, 0.0014, 0.0015, 0.0016, 0.0018, 0.0020, 0.0021, 0.0022, 0.0024, 0.0026, 0.0028, 0.0030, 0.0032, 0.0035, 0.0037, 0.0040, or 0.0042 g CO/100 g aqueous solution. Preferred ranges include, e.g., about 0.0010 to about 0.0030 g CO/100 g liquid, about 0.0015 to about 0.0026 g CO/100 g liquid, or about 0.0018 to about 0.0024 g CO/100 g liquid. For water at 0° C., the saturation point is about 0.0044 g CO/100 g medium.

Any suitable liquid can be saturated to a set concentration of carbon monoxide via gas diffusers. Alternatively, premade solutions that have been quality controlled to contain set levels of carbon monoxide can be used. Accurate control of dose can be achieved via measurements with a gas permeable, liquid impermeable membrane connected to a carbon monoxide analyzer. Solutions can be saturated to desired effective concentrations and maintained at these levels. In both liquid and gaseous compositions, the inclusion of the inert gas helium can improve carbon monoxide delivery to the tissues of an organ.

Treatment of Patients with Carbon Monoxide

A patient can be treated with a carbon monoxide composition by any method known in the art of administering gases and/or liquids to patients. The present invention contemplates the administration of carbon monoxide in gaseous and/or liquid form to patients. Exemplary routes of administration include, but are not limited to systemic (e.g., by inhalation and/or ingestion) and topical to the patient's organs or tissues in situ (e.g., by ingestion, insufflation, and/or introduction into the abdominal cavity).

Dosing Regimens for Carbon Monoxide

Carbon monoxide is administered to the patient intra-operatively in an effective amount and at the time of reperfusion that results in a carboxyhemoglobin concentration of at least 7%. In one embodiment, the carboxyhemoglobin concentration is between about 7% and about 15%. In one embodiment, the patient is administered carbon monoxide at a dose ranging between about 2 mg/kg to about 3 mg/kg for a sufficient time period that results in an effective carboxyhemoglobin concentration. In certain embodiments, the patient is administered carbon monoxide at a dose of 3 mg/kg for a sufficient time period that results in an effective carboxyhemoglobin concentration.

In certain embodiments of the methods provided herein for enhancing organ function following transplant thereof, carbon monoxide is administered to the patient at the time around reperfusion.

Systemic Delivery of Carbon Monoxide

Gaseous carbon monoxide compositions can be delivered systemically to a patient undergoing a transplant. Typically, such gaseous carbon monoxide compositions are administered by inhalation through the mouth or nasal passages to the lungs, where the carbon monoxide is readily absorbed into the patient's bloodstream. The concentration of active compound (CO) utilized in the therapeutic gaseous composition will depend on absorption, distribution, inactivation, and excretion (generally, through respiration) rates of the carbon monoxide as well as other factors known to those of skill in the art. It is to be further understood that for any particular subject, specific dosage regimens may be adjusted over time according to the individual need and the professional judgment of the person administering or supervising the administration of the compositions. Acute, sub-acute and chronic administration of carbon monoxide is contemplated by the present invention, depending upon, e.g., the severity or persistence of the disease or condition of the patient. Carbon monoxide can be delivered to the patient for a time sufficient to treat the disease or condition and exert the intended pharmacological or biological effect.

The following are examples of some methods and devices that can be utilized to administer gaseous carbon monoxide compositions to patients.

Ventilators: Carbon monoxide (concentrations can vary) can be purchased mixed with air or another oxygen-containing gas in a standard tank of compressed gas (e.g., 21% $O_2$, 79% $N_2$). It is non-reactive, and the concentrations that are required for the methods of the present invention are well below the combustible range (10% in air). In a hospital setting, the gas presumably will be delivered to the bedside where it will be mixed with oxygen or house air in a blender to a desired concentration. The patient will inhale the gas mixture through a ventilator, which will be set to a flow rate based on patient comfort and needs. This is determined by pulmonary graphics (i.e., respiratory rate, tidal volumes, etc.). Fail-safe mechanism(s) to prevent the patient from unnecessarily receiving greater than desired amounts of carbon monoxide can be designed into the delivery system. The patient's carbon monoxide level can be monitored by studying (1) carboxyhemoglobin (COHb), which can be measured in venous blood, and (2) exhaled carbon monoxide collected from a side port of the ventilator. Carbon monoxide exposure can be adjusted based upon the patient's health status and on the basis of the markers. If necessary, carbon monoxide can be washed out of the patient by switching to 100% $O_2$ inhalation. Carbon monoxide is not metabolized; thus, whatever is inhaled will ultimately be exhaled except for a very small percentage that is converted to $CO_2$. Carbon monoxide can also be mixed with any level of $O_2$ to provide therapeutic delivery of carbon monoxide without consequential hypoxic conditions.

Face Mask and Tent: A carbon monoxide-containing gas mixture is prepared as above to allow inhalation by the patient using a facemask or tent. The concentration inhaled can be changed and can be washed out by simply switching over to 100% $O_2$. Monitoring of carbon monoxide levels would occur at or near the mask or tent with fail-safe mechanism(s) that would prevent too high of a concentration of carbon monoxide from being inhaled.

Portable Inhaler: Compressed carbon monoxide can be packaged into a portable inhaler device and inhaled in a metered dose, for example, to permit intermittent treatment of a recipient who is not in a hospital setting. Different concentrations of carbon monoxide could be packaged in the containers. The device could be as simple as a small tank (e.g., under 5 kg) of appropriately diluted CO with an on-off valve and a tube from which the patient takes a whiff of CO according to a standard regimen or as needed.

Intravenous Artificial Lung: An artificial lung (a catheter device for gas exchange in the blood) designed for $O_2$ delivery and $CO_2$ removal can be used for carbon monoxide delivery. The catheter, when implanted, resides in one of the large veins and would be able to deliver carbon monoxide at given concentrations either for systemic delivery or delivery to a local site. The delivery can be a local delivery of a high concentration of carbon monoxide for a short period of time at a specific site (this high concentration would rapidly be diluted out in the bloodstream), or a relatively longer systemic exposure to a lower concentration of carbon monoxide (see, e.g., Hattler et al., *Artif Organs*, 18(11):806-812 (1994); and Golob et al., *ASAIO J*, 47(5):432-437 (2001)).

Normobaric Chamber: In certain instances, it would be desirable to expose the whole patient to carbon monoxide. The patient would be inside an airtight chamber that would be flooded with carbon monoxide (at a level that does not endanger the patient, or at a level that poses an acceptable risk without the risk of bystanders being exposed). Upon completion of the exposure, the chamber could be flushed with air (e.g., 21% $O_2$, 79% $N_2$), and samples could be analyzed by carbon monoxide analyzers to ensure no carbon monoxide remains before allowing the patient to exit the exposure system.

Aqueous Solutions: The present invention further contemplates that aqueous solutions comprising carbon monoxide can be created for systemic delivery to a patient (e.g., for oral delivery) and/or by injection into the body (e.g., intravenously, intra-arterially, intraperitoneally and/or subcutaneously).

Use of Additional Agent(s) for Therapeutic Effect

Also contemplated by the present invention is the induction or expression of hemeoxygenase-1 (HO-1) in conjunction with administration of carbon monoxide. HO-1 can be provided to a patient by inducing or expressing HO-1 in the patient, or by administering exogenous HO-1 directly to the patient. As used herein, the term "induce(d)" means to cause increased production of a protein, e.g., HO-1, in isolated cells or the cells of a tissue, organ or animal using the cells' own endogenous (e.g., non-recombinant) gene that encodes the protein. HO-1 can be induced in a patient, e.g., a donor and/or recipient, by any method known in the art. For example, production of HO-1 can be induced by hemin, by iron protoporphyrin, or by cobalt protoporphyrin. A variety of non-heme agents including heavy metals, cytokines, hormones, nitric oxide, $COCl_2$, endotoxin and heat shock are also strong inducers of HO-1 expression (Otterbein et al., *Am J Physiol Lung Cell Mol Physiol*, 279:L1029-L1037 (2000); Choi et al., *Am J Respir Cell Mol Biol*, 15:9-19 (1996); Maines, *Annu Rev Pharmacol Toxicol*, 37:517-554 (1997); and Tenhunen et at, *J Lab Clin Med*, 75:410-421 (1970)). HO-1 is also highly induced by a variety of agents and conditions that create oxidative stress, including hydrogen peroxide, glutathione depletors, UV irradiation and hyperoxia (Choi et al., *Am J Respir Cell Mol Biol*, 15:9-19 (1996); Maines, *Annu Rev Pharmacol Toxicol*, 37:517-554 (1997); and Keyse et al., *Proc Natl Acad Sci USA*, 86:99-103 (1989)). A "pharmaceutical composition comprising an inducer of HO-1" means a pharmaceutical composition containing any agent capable of inducing HO-1 in a patient, e.g., any of the agents described above, e.g., hemin, iron protoporphyrin, and/or cobalt protoporphyrin.

HO-1 expression in a cell can be increased via gene transfer. As used herein, the term "express(ed)" means to cause increased production of a protein, e.g., HO-1 or ferritin, in isolated cells or the cells of a tissue, organ or animal using an exogenously administered gene (e.g., a recombinant gene). The HO-1 or ferritin is preferably of the same species (e.g., human, mouse, rat, etc.) as the transplant recipient, in order to minimize any immune reaction. Expression could be driven by a constitutive promoter (e.g., cytomegalovirus promoters) or a tissue-specific promoter (e.g., milk whey promoter for mammary cells or albumin promoter for liver cells). An appropriate gene therapy vector (e.g., retrovirus, adenovirus, adeno associated virus (AAV), pox (e.g., vaccinia) virus, human immunodeficiency virus (HIV), the minute virus of mice, hepatitis B virus, influenza virus, Herpes Simplex Virus-1, and lentivirus) encoding HO-1 or ferritin would be administered to the patient orally, by inhalation, or by injection at a location appropriate for treatment of transplant rejection. Particularly preferred is local administration directly to the donor's organ, tissue or cells to be transplanted, or to the site of the transplant in the recipient. Similarly, plasmid vectors encoding HO-1 or apo-ferritin can be administered, e.g., as naked DNA, in liposomes, or in microparticles.

Further, exogenous HO-1 protein can be directly administered to a patient by any method known in the art. Exogenous HO-1 can be directly administered in addition to, or as an alternative, to the induction or expression of HO-1 in the patient as described above. The HO-1 protein can be delivered to a patient, for example, in liposomes, and/or as a fusion protein, e.g., as a TAT-fusion protein (see, e.g., Becker-Hapak et al., *Int J Colorectal Dis*, 16(4):247-256, (2001)).

Alternatively or in addition, any of the products of metabolism by HO-1, e.g., bilirubin, biliverdin, iron, and/or ferritin, can be administered to a patient in conjunction with, or instead of, carbon monoxide in order to prevent or treat the disorder. Further, the present invention contemplates that iron-binding molecules other than ferritin, e.g., desferoxamine (DFO), iron dextran, and/or apoferritin, can be administered to the patient. Any of the above compounds can be administered to the patient topically and/or systemically.

Though not meant to be bound by theory, it is believed that administration of carbon monoxide dosing regimens of the present invention result in triggering of signaling pathways that provide a therapeutic effect. In particular, it is believed that administration of carbon monoxide dosing regimens of the present invention reduce ischemia reperfusion injury associated with organ transplant. Importantly, administration of carbon monoxide intra-operatively during transplant surgery is thought to increase organ function and survival thereof by providing a protective effect against reactive oxygen species which are most generated at that time.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Carbon Monoxide Dosing Regimens

Study subjects receive either (i) 12-48 hours post-operatively following renal transplant, a single dose of placebo (i.e., $O_2$ 30% in nitrogen) or carbon monoxide (Covox 12 mg/L) at 0.7 mg/kg or 2 mg/kg via inhalation for a time period of 1 hour, or (ii) intra-operatively during renal transplant surgery (at the time of re-anastomosis), a dose of placebo (i.e., $O_2$ 30% in nitrogen), 2 mg/kg or 3 mg/kg carbon monoxide via inhalation for a time period of 1 hour.

Dose-Dependency of COHb Exposure

Figure 1A:
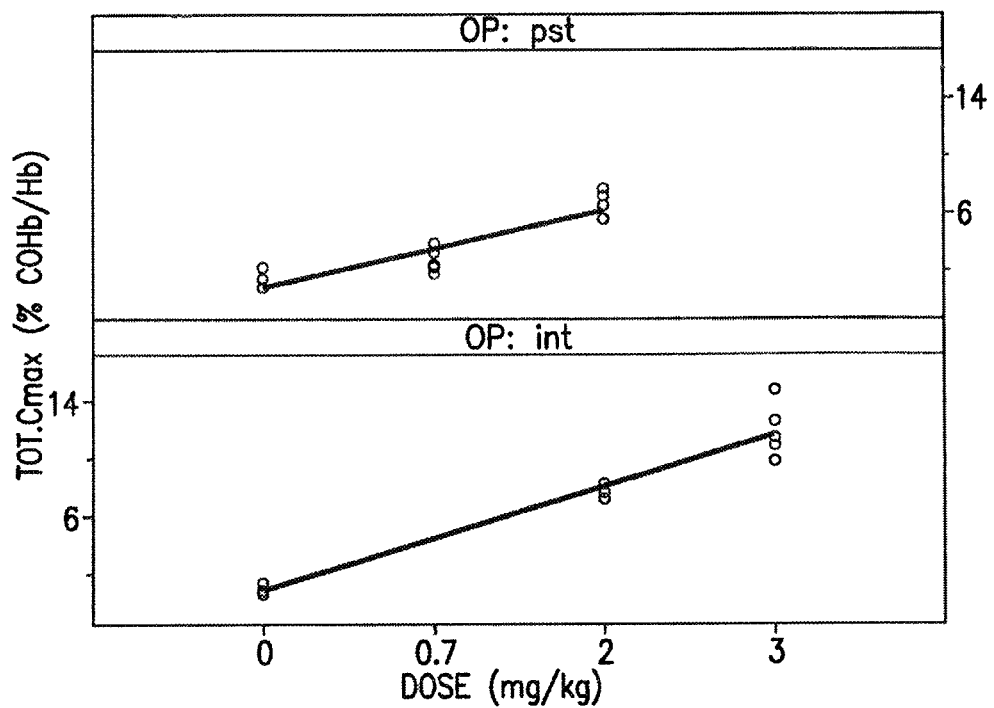
FIG. 1A illustrates the dose-dependency of the carboxyhemoglobin concentration based on total COHb (expressed as % COHb/Hb) when carbon monoxide was given either at 12-48 hours after transplant surgery (post-operatively, referred to therein as "OP:pst") or during surgery (intra-operatively, referred to therein as "OP:int"). Post-operative doses include placebo (i.e., $O_2$ 30% in nitrogen), 0.7 mg/kg or 2 mg/kg carbon monoxide via inhalation for a time period of 1 hour. Intra-operative doses include placebo (i.e., $O_2$ 30% in nitrogen), 2 mg/kg or 3 mg/kg carbon monoxide via inhalation for a time period of 1 hour.
Figure 1B:
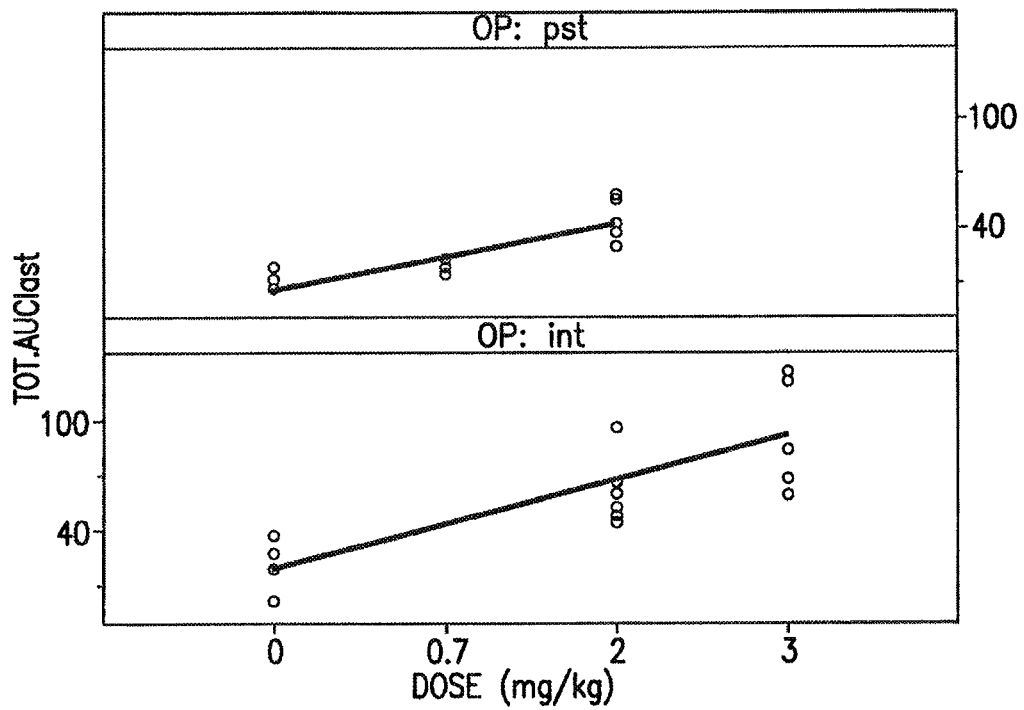
FIG. 1B illustrates the dose-dependency of the area under the blood concentration-time curve calculated to the last measured concentration ($AUC_{0-t}$) of carboxyhemoglobin based on total COHb (expressed as % COHb/Hb) when carbon monoxide was given either at 12-48 hours after transplant surgery (post-operatively, referred to therein as "OP:pst") or during surgery (intra-operatively, referred to therein as "OP:int"). Post-operative doses include placebo (i.e., $O_2$ 30% in nitrogen), 0.7 mg/kg or 2 mg/kg carbon monoxide via inhalation for a time period of 1 hour. Intra-operative doses include placebo (i.e., $O_2$ 30% in nitrogen), 2 mg/kg or 3 mg/kg carbon monoxide via inhalation for a time period of 1 hour.

COHb exposure is measured using conventional methods. For example, COHb exposure can be ascertained by measuring the amount present in venous blood using a device known as a CO-OXI meter. For both post- and intra-operative dosing regimens, dose-dependency of COHb Cmax and AUC is evaluated, the results of which are shown graphically in FIGS. 1A and 1B. Notably, % COHb/Hb increased with an increase in the dose of inhaled carbon monoxide in an approximately proportional manner. Based on these results as well as previous studies in healthy volunteers (data not shown), COHb pharmacokinetics are used as a surrogate marker for systemic carbon monoxide exposure.

Pharmacokinetics of Dosing Regimens

In post-operatively treated subjects, $C_{max}$ values (Mean±SD) of COHb were 2.77±0.77% at 0.7 mg/kg (n=6) ranging from 1.8% to 3.9% and 6.7±0.71% at 2 mg/kg (n=6) ranging from 5.6 to 7.7%. The elimination $t_{1/2}$ of COHb in CO treated subjects ranged from 2.2 to 9.9 hours. The COHb levels in placebo subjects ranged from 0.8 to 2.2%.

Key pharmacokinetic parameters of intra-operatively treated subjects are summarized in Table 1 below.

TABLE 1

| | | Based on Total COHb | | | Based on Net COHb* | | | CL/F | |
|---|---|---|---|---|---|---|---|---|---|
| Dose (mg/kg) | Subject | $C_{max}$ (%) | $T_{max}$ (hr) | $AUC_{0-t}$ (% * hr) | $C_{max}$ (%) | $AUC_{0-t}$ (% * hr) | Vss/F (mg/kg/%) | (mg/kg/ (% * h)) | $T_{1/2}$ (hr) |
| 0 | A | 1.3 | 6 | NA | NA | NA | NA | NA | NA |
| | B | 0.6 | 48 | NA | NA | NA | NA | NA | NA |
| | C | 0.8 | 0 | NA | NA | NA | NA | NA | NA |
| | D | 1.2 | 8 | NA | NA | NA | NA | NA | NA |
| | Mean | 0.975 | 15.5 | NA | NA | NA | NA | NA | NA |
| | Std Dev | 0.33 | 21.9 | NA | NA | NA | NA | NA | NA |
| 2.0 (intra- | E | 7.5 | 1.5 | 52.36 | 6 | 38.52 | 0.27 | 0.0519 | 3.59 |
| | F | 7.4 | 1 | 45.15 | 6.8 | 22.38 | 0.27 | 0.0894 | 2.19 |
| | G | 8.3 | 1 | 60.41 | 8.3 | 62.73 | 0.32 | 0.0319 | 8.04 |
| | H | 7.2 | 1 | 48.25 | 7.2 | 49.71 | 0.24 | 0.0402 | 5.06 |
| | I | 7.6 | 1 | 96.41 | 7.1 | 77.66 | 0.38 | 0.0258 | 12.12 |
| | J | 7.7 | 1 | 66.43 | 7.2 | 44.28 | 0.22 | 0.0452 | 3.69 |
| | Mean | 7.62 | 1.08 | 61.50 | 7.1 | 49.21 | 0.282 | 0.0474 | 5.78 |
| | Std Dev | 0.38 | 0.2 | 18.82 | 0.74 | 19.24 | 0.057 | 0.0226 | 3.68 |
| 3.0 (intra- | K | 10.9 | 1.08 | 84.26 | 10.8 | 84.44 | 0.458 | 0.0355 | 6.93 |
| | L | 14.8 | 0.75 | 59.33 | 13.1 | 30.65 | 0.12 | 0.0979 | 0.65 |
| | M | 9.8 | 1 | 68.04 | 9.5 | 52.93 | 0.378 | 0.0567 | 6.66 |

TABLE 1-continued

| | | Based on Total COHb | | | Based on Net COHb* | | | CL/F | |
|---|---|---|---|---|---|---|---|---|---|
| Dose (mg/kg) | Subject | $C_{max}$ (%) | $T_{max}$ (hr) | $AUC_{0-t}$ (% * hr) | $C_{max}$ (%) | $AUC_{0-t}$ (% * hr) | Vss/F (mg/kg/%) | (mg/kg/ (% * h)) | $T_{1/2}$ (hr) |
| | N | 11.4 | 1 | 121.64 | 9.9 | 65.19 | 0.331 | 0.046 | 5.97 |
| | O | 12.6 | 1 | 126.38 | 11.5 | 78.47 | 0.482 | 0.0382 | 8.47 |
| | Mean | 11.9 | 0.967 | 91.93 | 11.0 | 62.34 | 0.354 | 0.0549 | 5.74 |
| | Std Dev | 1.9 | 0.126 | 30.67 | 1.4 | 21.50 | 0.144 | 0.0254 | 2.99 |

*COHb levels were subtracted from pre-dose level.

The COHb levels (mean±SD) were 7.62±0.38% (7.2-8.3%) at 2 mg/kg (n=6) and 11.9±1.9% (9.8-14.8%) at 3 mg/kg (n=5). In placebo subjects, COHb levels during surgery (intra-operative) ranged from 0.6 to 1.3%, similar to those with spontaneous breathing (post-operative). In the intra-operative subjects, the net gain of COHb from CO inhalation (subtracted from the pre-dose levels) peaked around 1 hour with $C_{max}$ of 7.1±0.74% (2 mg/kg) and 11.0±1.4% (3 mg/kg). The elimination $t_{1/2}$ estimated from the net COHb levels averaged about 6 hours for both dose levels.

Enhancement of Transplanted Organ Function

Figure 2:
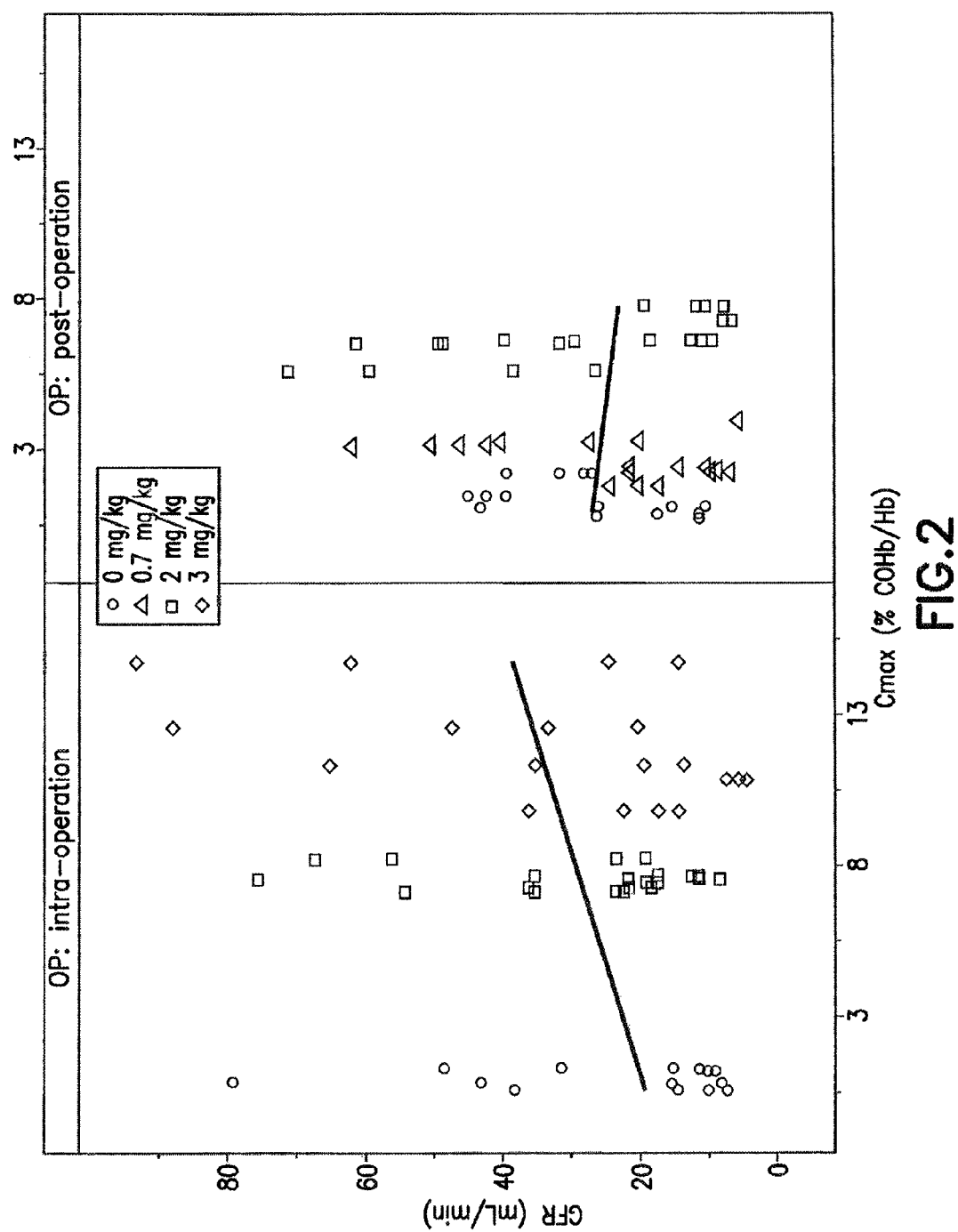
FIG. 2 illustrates the relationship between calculated glomerular filtration rate (GFR) on Day 1 and Day 2 and carboxyhemoglobin concentration expressed as % COHb/Hb for all subjects. Left panel (intra-operatively treated subjects) demonstrates that increased COHb is related to improved renal function (GFR). Right panel (post-operatively treated subjects) demonstrates that increased COHb is not related to the improvement of GFR, suggesting that carbon monoxide with the post-operative regimen has no beneficial effect on the renal function of renal transplant recipients.
Figure 3:
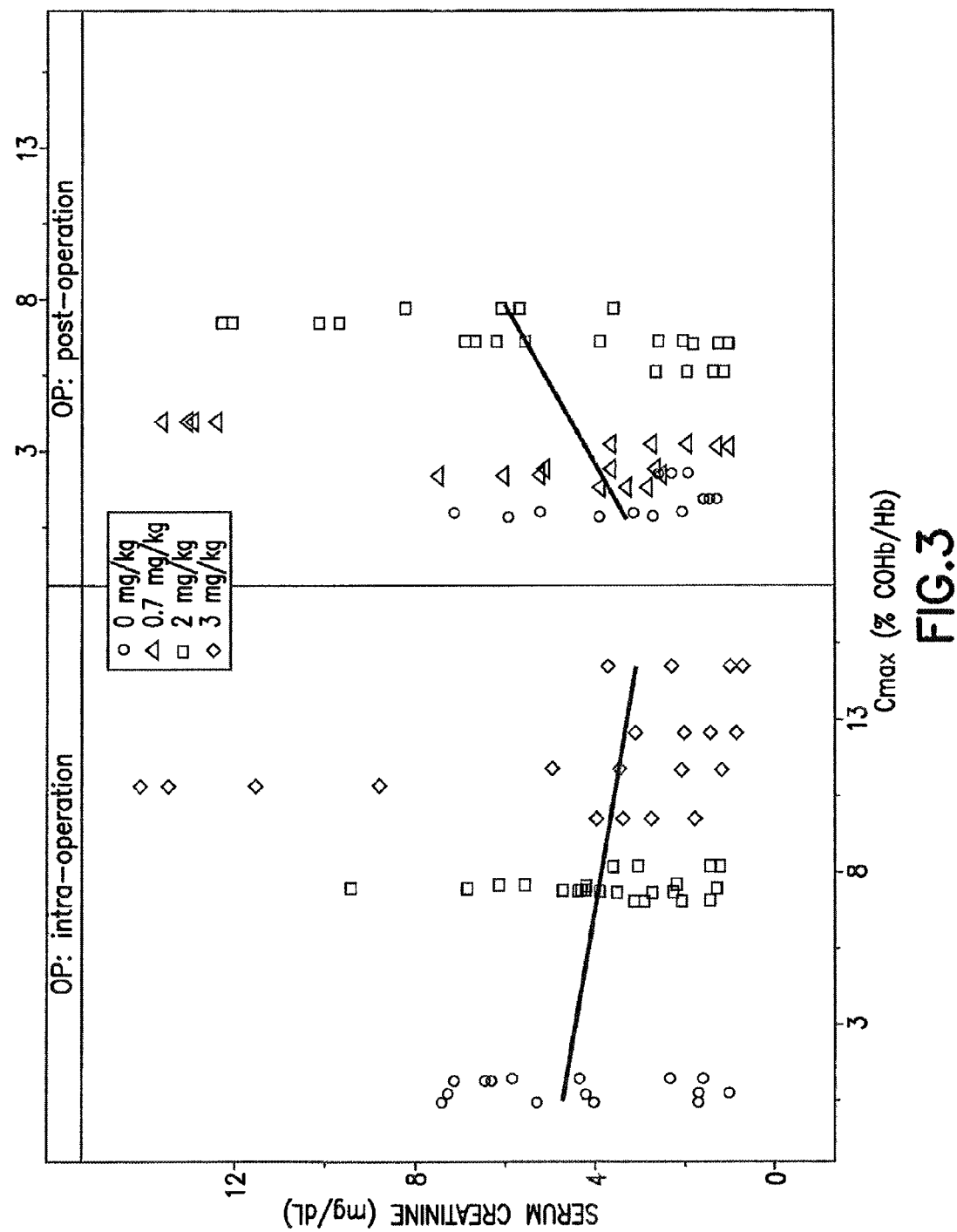
FIG. 3 illustrates the relationship between the serum creatinine level measured on Day 2 and carboxyhemoglobin concentration expressed as % COHb/Hb. Left panel (intra-operatively treated subjects) demonstrates that increased COHb is related to improved renal function (decreased serum creatinine). Right panel (post-operatively treated subjects) demonstrates that increased COHb did not improve the renal function (increased serum creatinine), suggesting that carbon monoxide with the post-operative regimen has no beneficial effect on the renal functions of renal transplant recipients.

Organ function is assessed in subjects using pharmacodynamic markers representing renal functions. In particular, serum creatinine (SCr) levels are measured (using conventional methods) and glomerular filtration rate (GFR) is calculated via MDRD (GFR (mL/min/1.73 m2)=175×(Scr)−1.154× (Age)−0.203×(0.742 if female)×(1.212 if African American); as described by Levey et al., "Chronic Kidney Disease Epidemiology Collaboration. Using standardized serum creatinine values in the modification of diet in renal disease study equation for estimating glomerular filtration rate," *Ann Intern Med*, 145(4):247-254 (2006)). Importantly, when carbon monoxide is given during surgery (intra-operatively), treatment with carbon monoxide improves renal function in a dose-dependent manner as indicated by a positive correlation between COHb and markers of renal function (GFR and Scr) illustrated in the left panels of FIGS. 2 and 3, respectively. When carbon monoxide is given 12-48 hours after the surgery, it does not improve renal function as illustrated in the right panels of FIGS. 2 and 3. These findings suggest that carbon monoxide must be present at the time of reperfusion to exert its cytoprotective effect and to prevent injuries caused by reperfusion.

Safety of Carbon Monoxide Dosing Regimens

Figure 4:
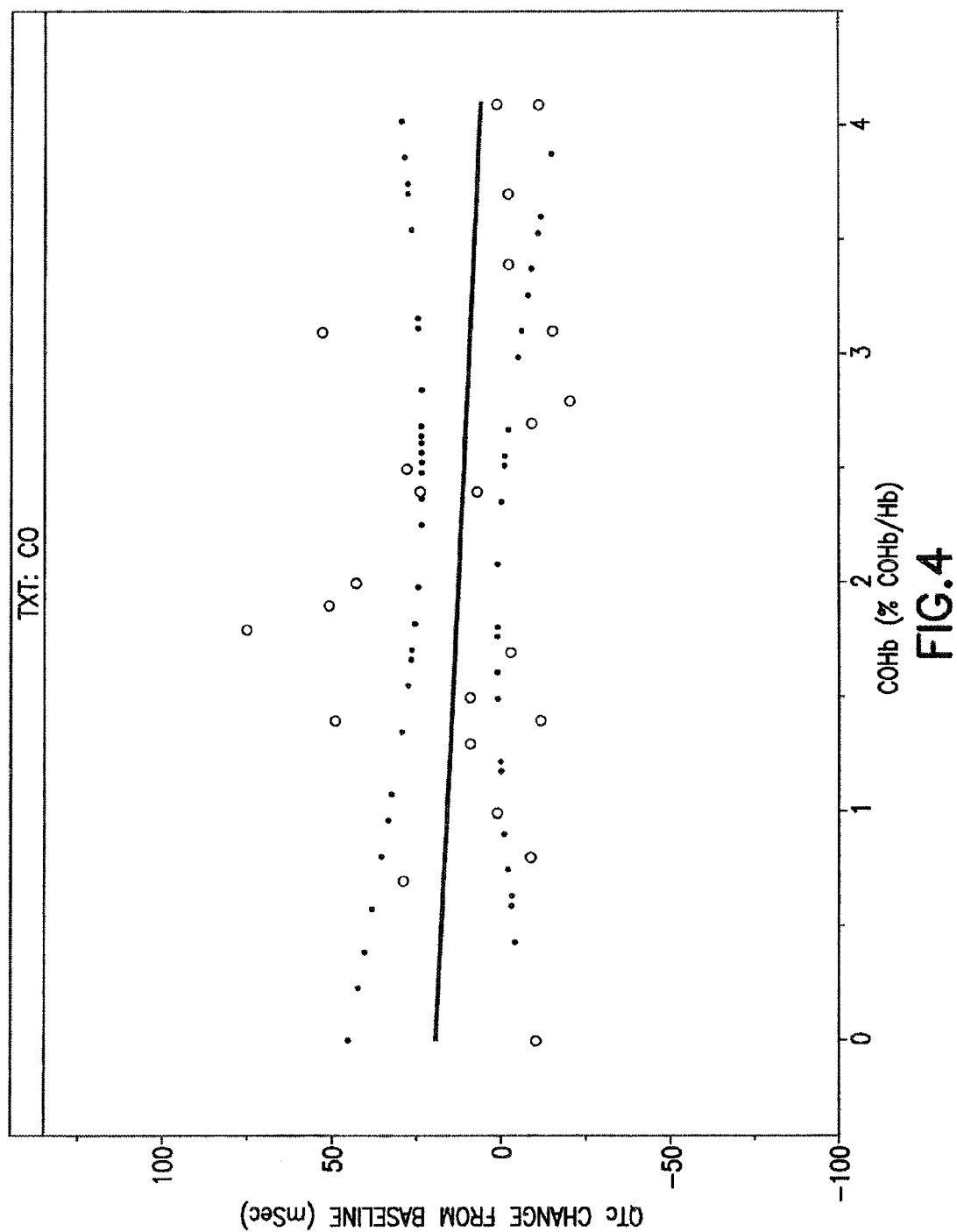
FIG. 4 illustrates the relationship between the COHb level (expressed as % COHb/Hb) and QTc change from baseline at 8 hours following carbon monoxide inhalation (both intra-operatively and post-operatively treated). Specifically, subjects were administered either (i) 12-48 hours post-operatively following renal transplant a dose of 0.7 mg/kg or 2 mg/kg carbon monoxide via inhalation for a time period of 1 hour or (ii) intra-operatively during renal transplant surgery 2 mg/kg or 3 mg/kg carbon monoxide via inhalation for a time period of 1 hour. The negative correlation demonstrates that carbon monoxide does not have an effect on QT prolongation at a dose level up to 3 mg/kg.

All renal transplant recipients receiving carbon monoxide up to 3 mg/kg carbon monoxide (both intra-operatively and post-operatively dosed) are evaluated for safety. At all dose levels evaluated, CO is found to be well tolerated. Incidence of cardiovascular and neurological AEs is comparable between CO and placebo treated subjects. In particular, no ECG changes observed on heart rate, PR interval, QRS duration or QTcF duration. Likewise, no evidence observed on new morphological changes or new infarction potentials. Additionally, CO treatment does not show any negative impact on neurocognitive functions. The most sensitive organs to carbon monoxide poisoning are heart and brain. As presented herein, the relationship between carbon monoxide exposure (COHb) and cardiovascular function (i.e., QTc) at 8 hours post-treatment of subjects receiving inhaled carbon monoxide or placebo (FIG. 4) is assessed via a pharmacokinetic-pharmacodynamic (PKPD) approach. Similarly, as presented herein, the relationship between subjects receiving one of various inhaled carbon monoxide doses or placebo and key neurocognitive functions (i.e., individual digit vigilance speed (FIG. 5), numeric working memory accuracy (FIG. 6) and picture recognition (FIG. 7)) up to 24 weeks post-treatment is assessed via a pharmacokinetic-pharmacodynamic (PKPD) approach.

PKPD analysis revealed a negative correlation between CO exposure and QTc (FIG. 4) and between CO exposure and neurocognitive functions (FIGS. 5, 6 and 7) in renal transplant recipients receiving up to 3 mg/kg carbon monoxide via inhalation for a time period of 1 hour. The negative correlations demonstrate that carbon monoxide is unlikely to cause QT prolongation and affect neurocognitive functions when given via inhalation for a time period of 1 hour at a dose of up to 3 mg/kg.

It will be appreciated by those skilled in the art that changes could be made to the embodiments described above without departing from the broad inventive concept thereof. It is understood, therefore, that this invention is not limited to the particular embodiments disclosed, but is intended to cover modifications that are within the spirit and scope of the invention, as defined by the appended claims.

Each document (including granted patents, published patent applications, and nonpatent publications such as journal articles) referred to in this application is incorporated in its entirety by reference for all purposes.

The invention claimed is:

1. A method for treating a patient in need thereof with carbon monoxide, comprising administering to the patient an effective amount of carbon monoxide that results in a carboxyhemoglobin concentration of between about 3% and about 15% without negative impact on cardiovascular and neurocognitive functions of the patient wherein carbon monoxide is administered via inhalation to the patient intra-operatively during organ transplant surgery, wherein the organ is kidney, in a single dose ranging between about 0.7 mg/kg to about 3 mg/kg for 1 hr.

2. The method of claim 1, wherein the patient is administered carbon monoxide at a dose ranging between about 2 mg/kg to about 3 mg/kg for 1 hr.

3. The method of claim 1, wherein the patient is administered carbon monoxide at a dose of 3 mg/kg for 1 hr.

4. The method of claim 1, further comprising administering an additional agent that has a therapeutic effect wherein the additional agent is a hemeoxygenase-1 or hemeoxygenase-1-affecting additional agent.

5. The method of claim 1, wherein carbon monoxide is administered to the patient in a gaseous form.

* * * * *

UNITED STATES PATENT AND TRADEMARK OFFICE
CERTIFICATE OF CORRECTION

| | |
|---|---|
| PATENT NO. | : 8,778,413 B2 |
| APPLICATION NO. | : 13/106437 |
| DATED | : July 15, 2014 |
| INVENTOR(S) | : Helen H. Usansky et al. |

It is certified that error appears in the above-identified patent and that said Letters Patent is hereby corrected as shown below:

On the Title Page at item (73) Assignee, the patent should read --INO Therapeutics LLC--.

Signed and Sealed this
Twenty-third Day of June, 2015

Michelle K. Lee
*Director of the United States Patent and Trademark Office*